United States Patent
Cohen-Erner

(10) Patent No.: US 9,638,644 B2
(45) Date of Patent: May 2, 2017

(54) MULTIPLE MODE INSPECTION SYSTEM AND METHOD FOR EVALUATING A SUBSTRATE BY A MULTIPLE MODE INSPECTION SYSTEM

(71) Applicant: CAMTEK LTD., Migdal Haemek (IL)

(72) Inventor: Moshe Cohen-Erner, Even Yehuda (IL)

(73) Assignee: CAMTEK LTD., Migdal Haemeq (IL)

( * ) Notice: Subject to any disclaimer, the term of this patent is extended or adjusted under 35 U.S.C. 154(b) by 142 days.

(21) Appl. No.: 14/445,086

(22) Filed: Jul. 29, 2014

(65) Prior Publication Data

US 2015/0042983 A1 Feb. 12, 2015

Related U.S. Application Data

(60) Provisional application No. 61/863,440, filed on Aug. 8, 2013.

(51) Int. Cl.
*G01N 21/95* (2006.01)
*G01N 21/956* (2006.01)
*G01N 21/88* (2006.01)

(52) U.S. Cl.
CPC ....... *G01N 21/9501* (2013.01); *G01N 21/956* (2013.01); *G01N 2021/8825* (2013.01)

(58) Field of Classification Search
CPC ...... G02B 21/125; G02B 21/10; G02B 21/12; G02B 21/14; G01N 2021/8825; G01N 21/9501; G01N 21/956
See application file for complete search history.

(56) References Cited

U.S. PATENT DOCUMENTS

| | | | | |
|---|---|---|---|---|
| 2,637,243 A * | 5/1953 | Marx | ............... | G02B 21/14 359/370 |
| 4,687,304 A * | 8/1987 | Piller | ............... | G02B 21/125 359/387 |
| 4,798,948 A * | 1/1989 | Neumann | ............. | G02B 5/22 250/201.3 |
| 4,881,802 A * | 11/1989 | Stankewitz | ......... | G02B 21/084 359/227 |
| 5,703,714 A * | 12/1997 | Kojima | ........... | G02B 21/06 250/201.3 |
| 6,727,993 B2 * | 4/2004 | Tomomatsu | ....... | G01N 21/8806 356/237.2 |
| 2004/0114219 A1 * | 6/2004 | Richardson | ......... | G01J 3/10 359/368 |
| 2004/0201837 A1 * | 10/2004 | Lange | ............ | G01N 21/9501 356/237.2 |
| 2007/0041091 A1 * | 2/2007 | Takeuchi | ............ | G02B 21/16 359/386 |
| 2007/0273945 A1 * | 11/2007 | Furman | ............ | G01N 21/8806 359/107 |
| 2008/0043324 A1 * | 2/2008 | Lytle | ............ | G02B 21/082 359/388 |

(Continued)

*Primary Examiner* — Michael P Lapage
(74) *Attorney, Agent, or Firm* — Reches Patents

(57) ABSTRACT

A multiple mode evaluation system that includes a multiple mode imager that is arranged to perform a single scan of a substrate while alternating between different optical modes thereby producing different sets of images of areas of the substrate, each set of images being associated with a single optical mode of image acquisition; wherein the different optical modes differ from each other by at least one optical characteristic.

5 Claims, 15 Drawing Sheets

(56) References Cited

U.S. PATENT DOCUMENTS

| | | | |
|---|---|---|---|
| 2008/0225298 A1* | 9/2008 | Fairley | G01N 21/8806 356/445 |
| 2013/0044202 A1* | 2/2013 | Kajiro | G02B 21/125 348/79 |
| 2013/0077159 A1* | 3/2013 | Tani | G02B 21/125 359/387 |

* cited by examiner

MULTIPLE MODE INSPECTION SYSTEM AND METHOD FOR EVALUATING A SUBSTRATE BY A MULTIPLE MODE INSPECTION SYSTEM

RELATED APPLICATIONS

This application claims priority from U.S. provisional patent 61/863,440 filing date Aug. 8, 2013 which is incorporated by reference.

BACKGROUND OF THE INVENTION

Inspection systems dedicated for optical inspection of substrates such as semiconductor wafer or printed circuit boards may scan (during different stages of the manufacturing process of the substrates) the substrates. Each scan is dedicated to a single optical mode.

There is a need to provide an inspection system that may provide information of various types per scan.

SUMMARY

According to an embodiment of the invention there may be provided multiple mode evaluation system that may include a multiple mode imager that may be arranged to perform a single scan of a substrate while alternating between different optical modes thereby producing different sets of images of areas of the substrate, each set of images being associated with a single optical mode of image acquisition; wherein the different optical modes differ from each other by at least one optical characteristic.

The different sets of images may cover overlapping areas of the substrate.

Images of different sets of images may be combined to provide a combined image.

Each point of the substrate may be associated with a pixel per each of the different optical modes.

At least two optical modes (of the different optical modes) may differ from each other by at least one out of polarization, angular coverage (collection angle, illumination angle, both collection and illumination angles, bright field, dark field and the like), wavelength, intensity or any other optical parameter.

The number of cameras of the multiple mode imager may equal the number of different optical modes or may differ from the number of different optical modes.

The multiple mode imager may include a movable optical element and an optical element movement module. The optical element movement module may be connected to the movable optical element and may be arranged to move the movable optical element and thereby cause the alternating of the multiple mode imager between the different optical modes of image acquisition.

The movable optical element may include different portions of different optical characteristics; wherein the movement of the movable optical element causes the different portions to enter, at different points of time, at least one optical path out of an illumination path and a collection path of the multiple mode imager.

The movable optical element may be arranged to move the moveable optical element by rotating the movable optical element.

The movable optical element may include different portions of different optical characteristics; wherein the rotation of the movable optical element places, at different points of time, the different portions within at least one of a collection path and an illumination path of the multiple mode imager.

The different portions may differ from each other by at least one out of polarization, reflectivity, wavelength filtering, spatial filtering, attenuation and the like.

The different portions may differ from each other by reflectivity.

The movable optical element may include a center and multiple spaced apart branches that extend from the center. Each branch may include a radiation reflecting element. A rotation of the movable optical element causes radiation reflecting elements attached to the spaced apart branches to enter, during only some of the different points of time, at least one optical path out of an illumination path and a collection path of the multiple mode imager.

Each radiation reflecting element, when entering the collection path directs radiation from the substrate towards a first camera of the multiple mode imager; wherein when any radiation reflecting element of the movable optical element may be not positioned within the collection path the radiation from the substrate may be directed towards a second camera of the multiple mode imager.

The first and second cameras may include a dark field camera and a bright field camera.

The number of spaced apart branches may two, three and the like.

The spaced apart branches may be arranged in radial symmetry.

The movable optical element may include a center and multiple spaced apart radiation reflecting elements, wherein movable optical element defines gaps between the spaced apart radiation reflecting elements. A rotation of the movable optical element may cause radiation reflecting elements attached to the spaced apart branches to enter, during only some of the different points of time, at least one optical path out of an illumination path and a collection path of the multiple mode imager.

The movable optical element may be arranged to move the moveable optical element by reciprocating the movable optical element.

The movable optical element may be arranged to move the moveable optical element by reciprocating the movable optical element between a first position in which the movable optical element may be outside an optical path out of a collection path and an illumination path of the multiple mode imager and a second position in which the movable optical element may be within the optical path. The first and second positions may differ from each other by an angle between the movable optical element and the substrate. Alternatively, the movable optical element may be moved, while alternating the optical modes, by a linear movement that does not change that angle.

The movable optical element may be arranged to move the movable optical element by a combination of clockwise and counterclockwise movements.

The movable optical element may be a mirror. The mirror may have a semi-circle shape or any other shape.

BRIEF DESCRIPTION OF THE INVENTION

One of the embodiments of the present invention will be understood and appreciated more fully from the following detailed description taken in conjunction with the drawings in which.

DETAILED DESCRIPTION OF THE INVENTION

Figure 1:
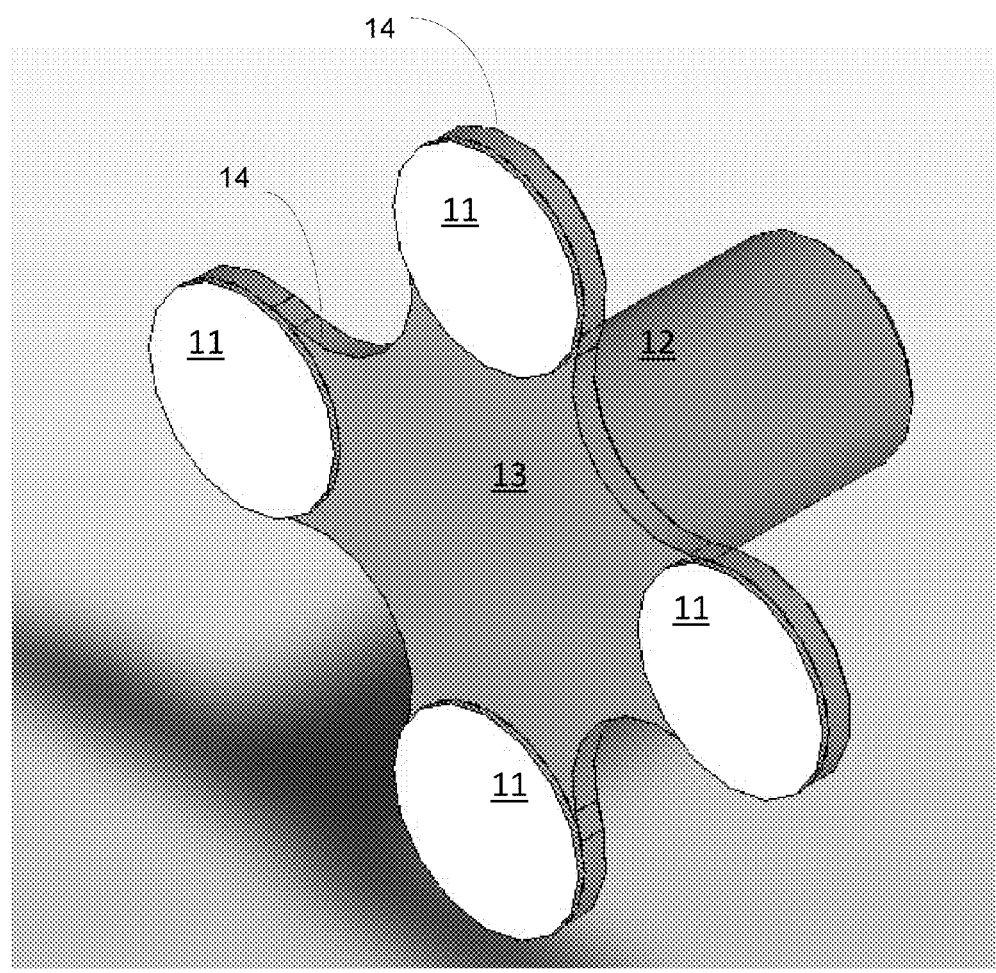
FIG. 1 illustrates a mirror according to an embodiment of the invention.

Because the apparatus implementing the present invention is, for the most part, composed of electronic components and circuits known to those skilled in the art, circuit details will not be explained in any greater extent than that considered necessary as illustrated above, for the understanding and appreciation of the underlying concepts of the present invention and in order not to obfuscate or distract from the teachings of the present invention.

In the following specification, the invention will be described with reference to specific examples of embodiments of the invention. It will, however, be evident that various modifications and changes may be made therein without departing from the broader spirit and scope of the invention as set forth in the appended claims.

The following text may refer to two optical modes and especially to a bright field mode and a dark field mode. It is noted that the system may alternate between more than two optical modes and that it may alternate between various optical modes that differ from bright field and dark field modes.

There is provided a system that is arranged to acquire images that include information from at least two perspectives, BF and DF taken separately. The images may be combined to provide a combined image.

During a scan of a substrate (or a selected portion) a set of images may be acquired for each optical mode. The set of images may include one or more images. For example, if the entire substrate is being scanned during the single scan each one of the different sets of images may include an image of the entire substrate or multiple images of different areas of the substrate.

There is a provided a system that may generate one or more combined images of a substrate, wherein each combined image represents at least two optical modes that are applied during one scan and receive multiple data on each point of the substrate.

The image acquisition rate for two optical modes may be same and with lateral shift. Two (or more) optical modes can have different illumination conditions (for an example BF and DF).

There is provided a system that alternates between at least two different optical modes, some alternating patterns are listed below:

a. BF-DF-BF-DF . . . ; BF=bright field, DF=dark field b. DFcolor1-DFcolor2-DF-color3 . . . ; multiple alternating DF modes that differ by color of illumination or collection.

c. BF-color1-BF-color2-BF-color3 . . . ;—multiple alternating BF modes that differ by wavelength of illumination or collection.

d. DFcolor1-BFcolor1-DFcolor1 . . . ; multiple alternating DF and BF modes that also differ from each other by wavelength of illumination or collection. DFcolor1-BFcolor2-DFcolor1-BF-color2 . . . multiple alternating DF and BF modes that also differ from each other by wavelength of illumination or collection e. DFcolor2-BFcolor2 . . . —multiple alternating DF and BF modes that also differ from each other by wavelength of illumination or collection.

The optical modes can differ from each other by at least one out of wavelength, polarization, intensity, angle, and any other optical characteristic.

The changing of polarization and/or wavelength or any other optical characteristic that is not related to the selection between BF and DF can be achieved by using a multiple mode imager that may alternate between the optical modes during a single scan of a substrate (or a selected portion of the substrate).

Each scan includes introduction of mechanical movement between optics and the substrate. The scan may also include optical and/or electrical scanning. A single scan of a substrate includes at least the mechanical movements required for scanning the entire substrate (or the selected portion). During the single scan the multiple mode imager acquired sets of images of areas the substrate. These areas may form the entire substrate or only a selected portion of the substrate. Each point of the substrate (or the selected portion) may be represented by different pixels that correspond to the different optical modes.

Figure 14:
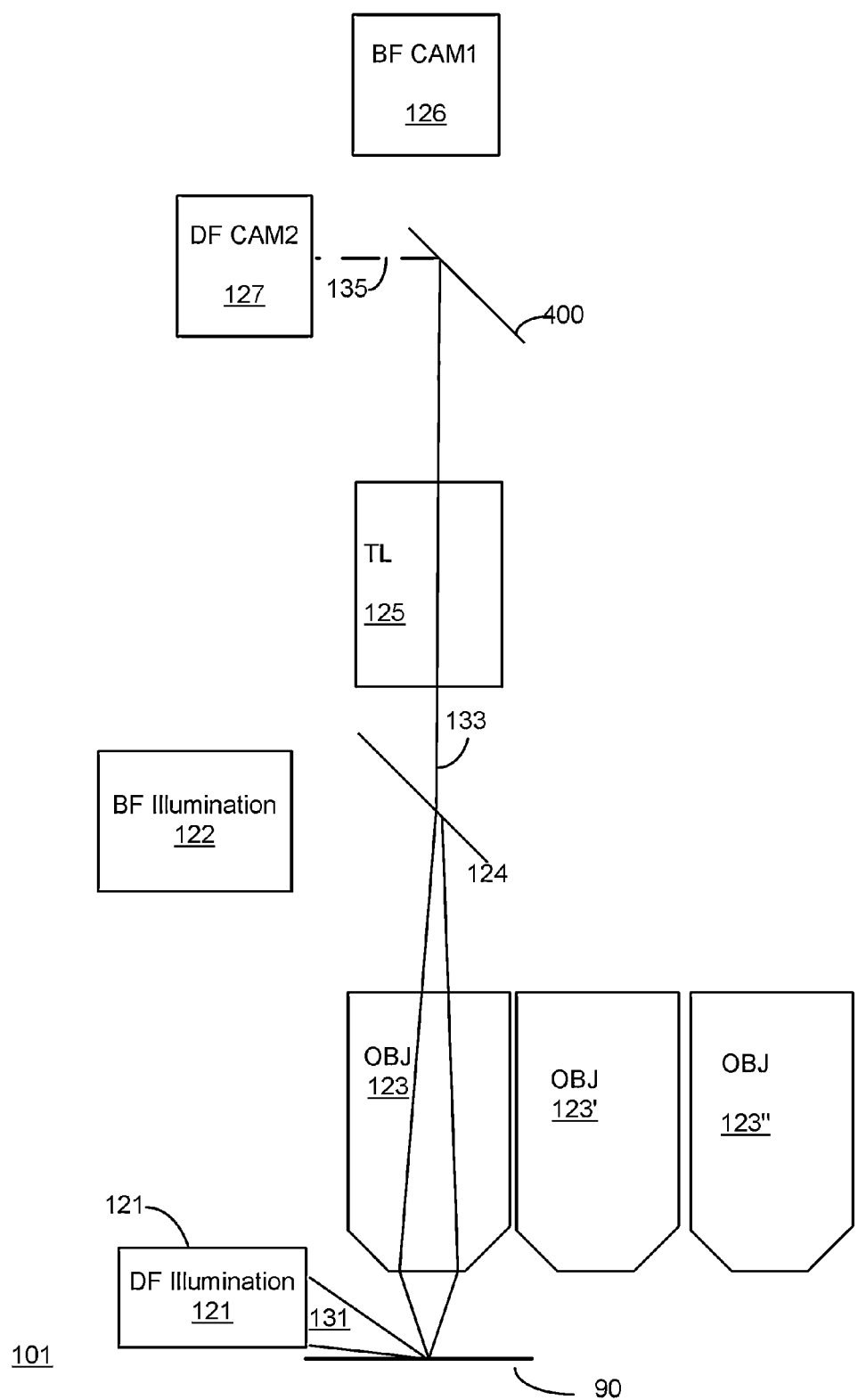
FIG. 14 illustrates a substrate and a multiple mode imager according to an embodiment of the invention.

The changing of optical modes may require, for example, moving or rotating movable optical elements such as filters, moving polarizers or any other optical elements or by using a variable optical optics element (such as a MEMS based element or such as optical element 400 of FIG. 14). Moving of filters may selectively affect the illuminating beam, and/or the collected beam.

One embodiment provides a system that includes optical paths such as a dark field light path and a bright field light path. Each path has a light sensor (DF sensor and BF sensor)—and the system includes a movable optical element (such as a mirror) that has reflecting segments and non-reflecting segments that are arranged in an interleaving manner so that once the movable optical element is rotated its segments enter, at different points of time, the collection path and distributes light to the DF sensor (when it is at certain positions) and it distributes light to the BF sensor (when it is at other positions).

The mirror can be connected to an axis that is used for rotating the mirror. This axis can be fixed (but allowed to rotate about the axis) and may be stable.

It is noted that the rotational movement can be replaced by a reciprocating movement or another movement.

The movable optical element can be inclined in relation to the optical axes of the DF sensor and the DF sensor.

According to an embodiment of the invention instead of rotating the movable optical element, the movable optical element can be moved or tilted between multiple positions—whereas the different positions facilitate a direction of light from the object to reach different cameras.

The movable optical element can be displaced in either a vertical position thus allowing the light to reach one sensor (for example) BF CAM 1 or in a tilted position in which it directs the light towards another sensor (for example DF CAM 2).

The movable optical element can be moved between these positions using a piezo movement mechanism.

According to another embodiment of the invention the system can be equipped with a single mirror coupled to a rotating mechanism that will allow rotation back and forwards.

It is noted that the system may include multiple movable optical elements wherein the alternating between modes may include moving more than a single movable optical element.

FIG. 1 illustrates a mirror 10 according to an embodiment of the invention.

It has four circular reflecting elements 11 that are held by a four-arm support element 13 and one axis 12. The four-arm support element 13 has four spaced apart branches 14. The circular reflecting elements 11 are spaced apart from each other. The optical axis of light reflected from an inspected is either reflected by one of the circular reflecting elements 11 or passes through the opening (gap) between the circular reflecting elements 11.

Figure 2:
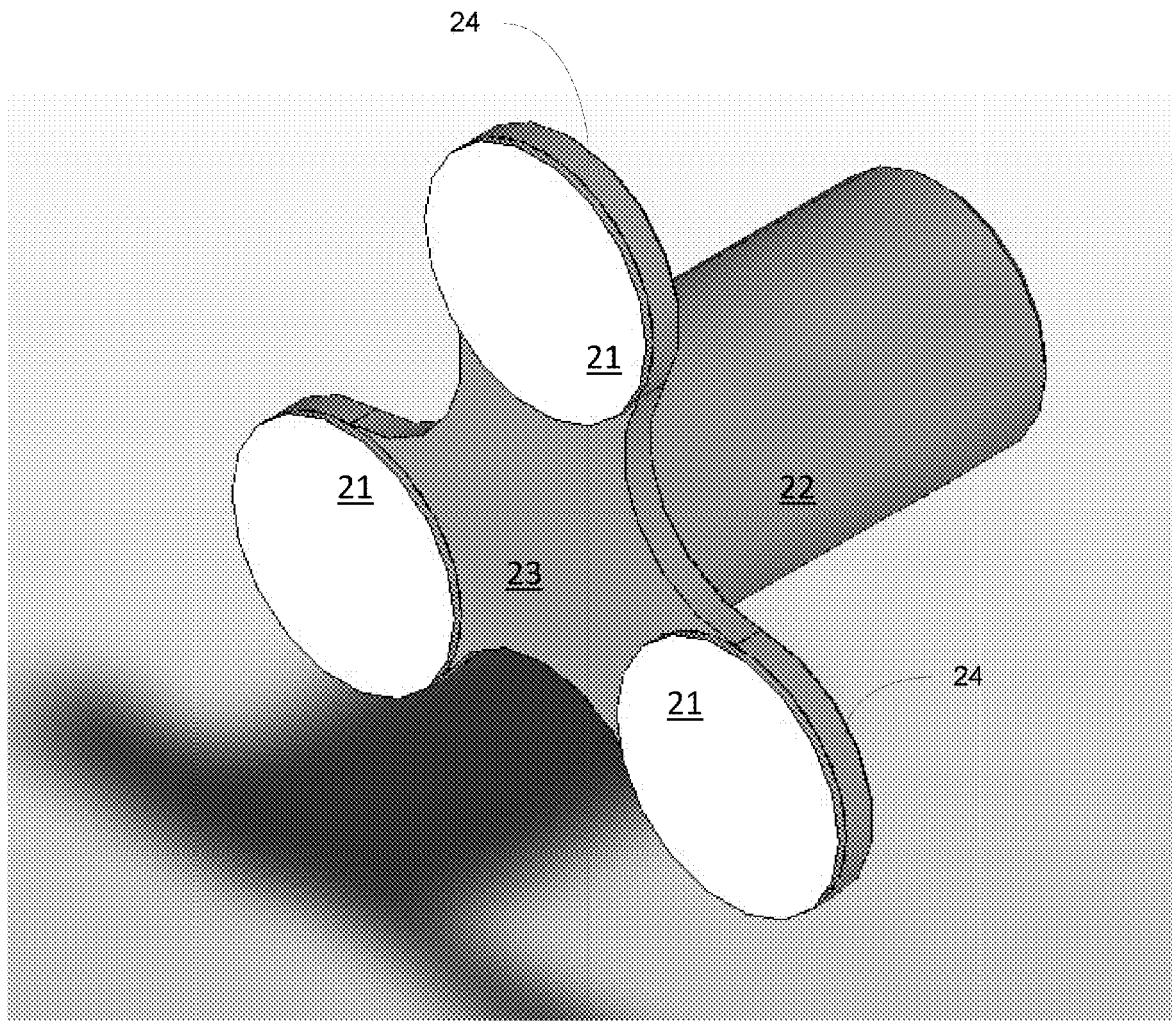
FIG. 2 illustrates a mirror according to an embodiment of the invention.

FIG. 2 shows a mirror according to an embodiment of the invention.

It has three circular reflecting elements 21 that are held by a three-arm support element 23 and one axis 22. The circular reflecting elements 21 are spaced apart from each other. The three-arm support element 23 has three spaced apart branches 24

The optical axis of light reflected from an inspected is either reflected by one of the circular reflecting elements 21 or passes through the opening (gap) between the circular reflecting elements 21.

Figure 3:
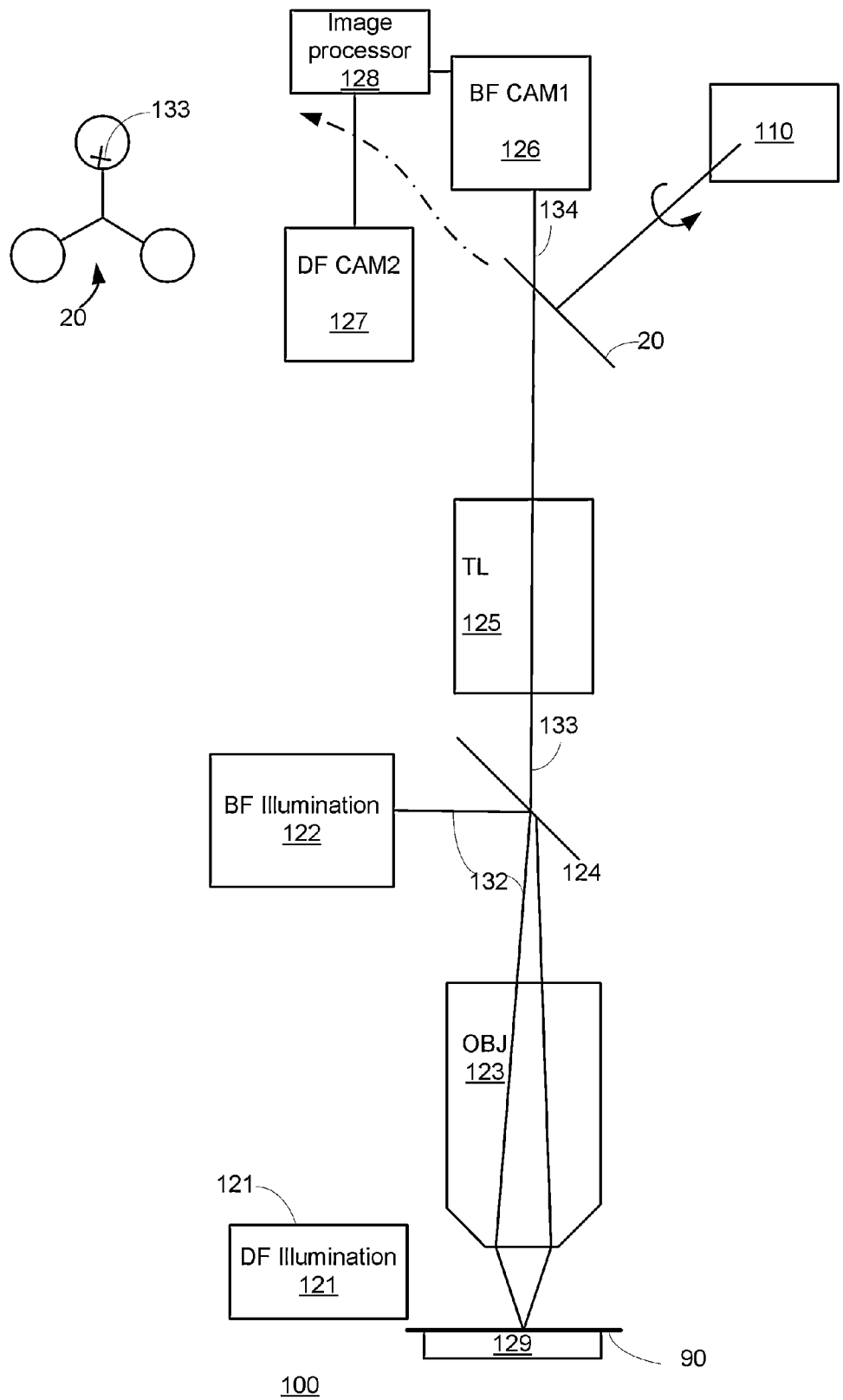
FIG. 3 illustrates a substrate and a multiple mode system according to an embodiment of the invention.
Figure 4:
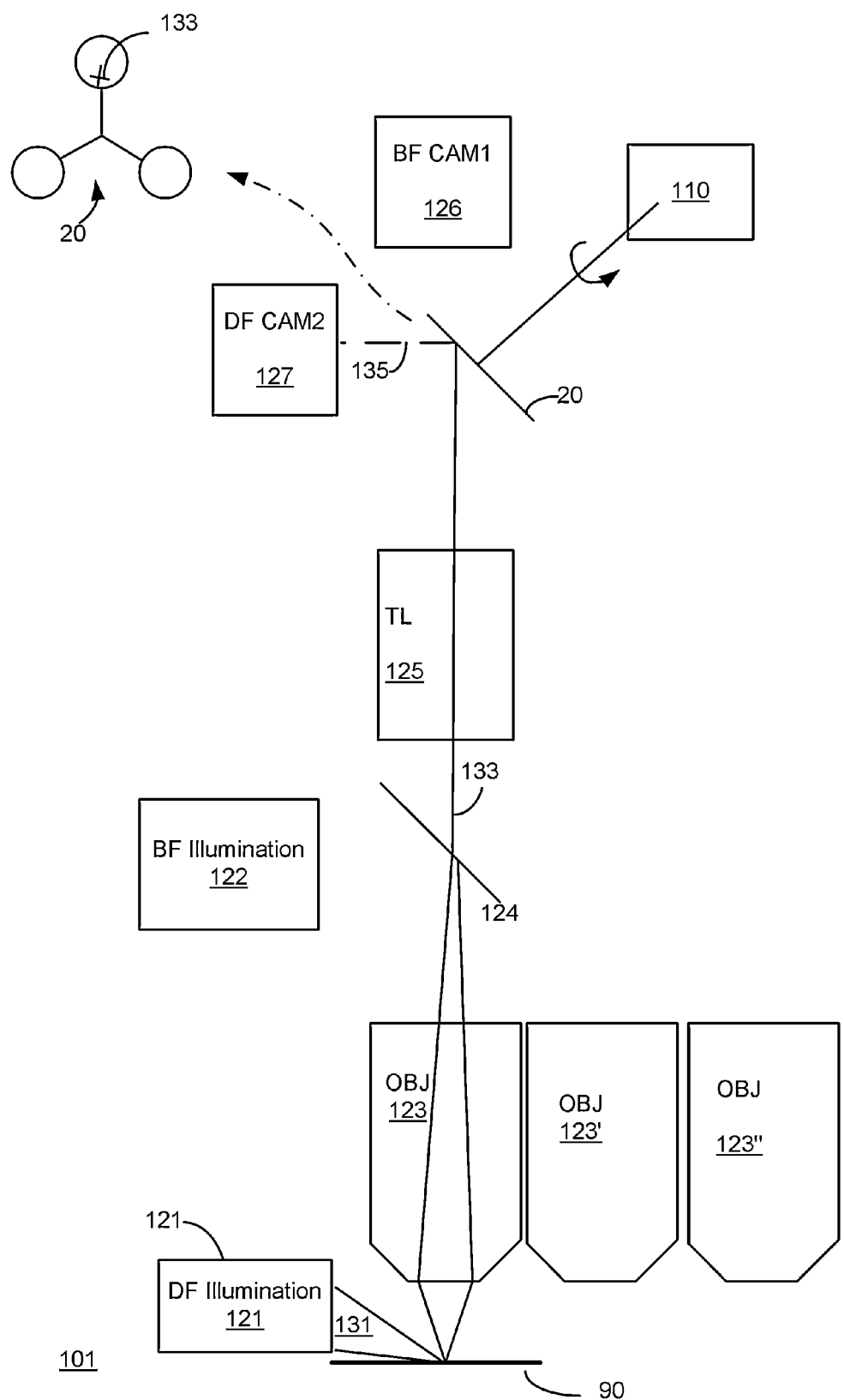
FIG. 4 illustrates a substrate and a multiple mode imager according to an embodiment of the invention.

FIG. 3 illustrates a substrate 90 and a multiple mode evaluation system 100 according to an embodiment of the invention. FIG. 4 illustrates a substrate 90 and a multiple mode imager 101 according to an embodiment of the invention.

For simplicity of explanation it is assumed that the multiple mode evaluation system 100 may include a multiple mode imager (denoted 101 in FIG. 4) and an image processor 128. It is noted that the image processor 128 may be included in the multiple mode imager, that the multiple mode imager may equal the multiple mode system and that the multiple mode imager may differ from the multiple mode system by one or more component other than the image processor 128.

The multiple mode images includes a dark field illumination source 121, a mechanical stage 129 (shown in FIG. 3 but not in FIG. 4) for supporting and moving the substrate 90 during a scan, an objective lens 123, a bright field illumination source 122, a beam splitter 124, a tube lens 125, bright field camera BF CAM 1 126, a dark field camera DF CAM 2 127, a first movable optical element such as mirror 20 of FIG. 2 and an optical element movement module 110 that is connected to mirror 20 and is arranged to rotate the mirror and thereby cause the alternating of the multiple mode imager between the different optical modes—which are bright field and dark field image acquisition modes.

Any other optical arrangement may be provided. For example there may not be a tube and/or an objective lens. There may be additional optical elements, and the like.

The dark field illumination source 121 illuminates the substrate 90 along a dark field illumination path 131 that is not normal to the substrate 90.

The bright field illumination source 121 illuminates a beam splitter 24 that directs the radiation through objective lens 123 and along a bright field illumination path 132 that is normal to the substrate 90.

Radiation from the substrate 90 propagates along a collection path 133 (also represented by x in an enlarged top view of the mirror 20 and the radiation) that is normal to the substrate. This radiation passes through the objective lens 123, the beam splitter 124 and the tube lens 125 to propagate towards mirror 20.

FIG. 3 illustrates points in time in which the radiation passes through gaps between the branches of mirror 20, along a bright field collection path 134, and impinges on bright field camera DF CAM1 126. In this state, the BF illumination pulse is 'on' and the DF illumination pulse is 'off'.

FIG. 4 illustrates other points in time in which the radiation impinges on light reflecting elements 21 of mirror 20 and are deflected to propagate, along a dark field collection path 135, to impinge on dark field camera DF CAM2 127.

It is noted that the angles of illumination and the arrangement of cameras may differ from those illustrated in FIGS. 3 and 4. For example, propagation through the gaps of mirror 20 may result in detection by dark field camera. Yet for another example the bright field illumination may not be normal to the substrate.

It is further noted that the multiple mode imager may include multiple objective lenses. FIG. 4 illustrates multiple objective lenses such as objective lens 123 as well as other objective lenses 123' and 123". The objective lenses may be replaced by using any mechanical arrangement such as but not limited to a turret.

It is noted that the operation of the bright field and dark field illumination sources may be controlled to be synchronized with the rotation of mirror so that bright field illumination pulses are generated when the mirror facilitates a propagation of light towards BF CAM1 126 and dark field illumination pulses are generated when the mirror facilitates a propagation of light towards DF CAM2 127. This is illustrated in FIG. 5.

Figure 5:
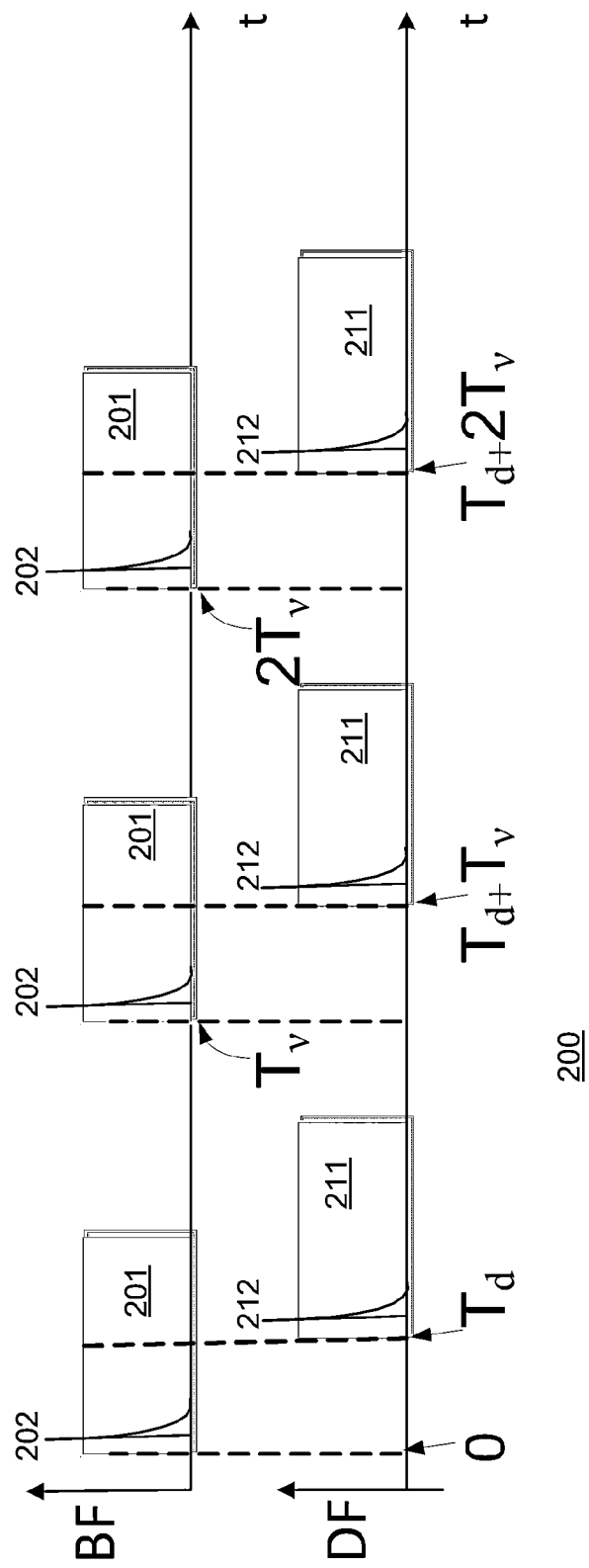
FIG. 5 is a timing diagram according to an embodiment of the invention.

FIG. 5 is a timing diagram 200 according to an embodiment of the invention. This timing diagram illustrates the alternation (time division multiplexing) between bright field and dark field image acquisition modes. Peaks 202 illustrate the acquisition of images by BF CAM1 126 while boxes 201 represent image processing and outputting (frame grabbing) periods of BF CAM1 126.

Peaks 212 illustrate the acquisition of images by DF CAM2 127 while boxes 211 represent image processing and outputting (frame grabbing) periods of DF CAM2 127.

Peaks 202 and 202 occur at spaced apart time periods while the image processing and outputting periods may partially overlap.

While FIG. 5 illustrates a duty cycle (period between consecutive peaks of the same camera) of $T_v$ and a time delay $T_d$ between the peaks of difference cameras other duty cycles may be provided.

Figure 6:
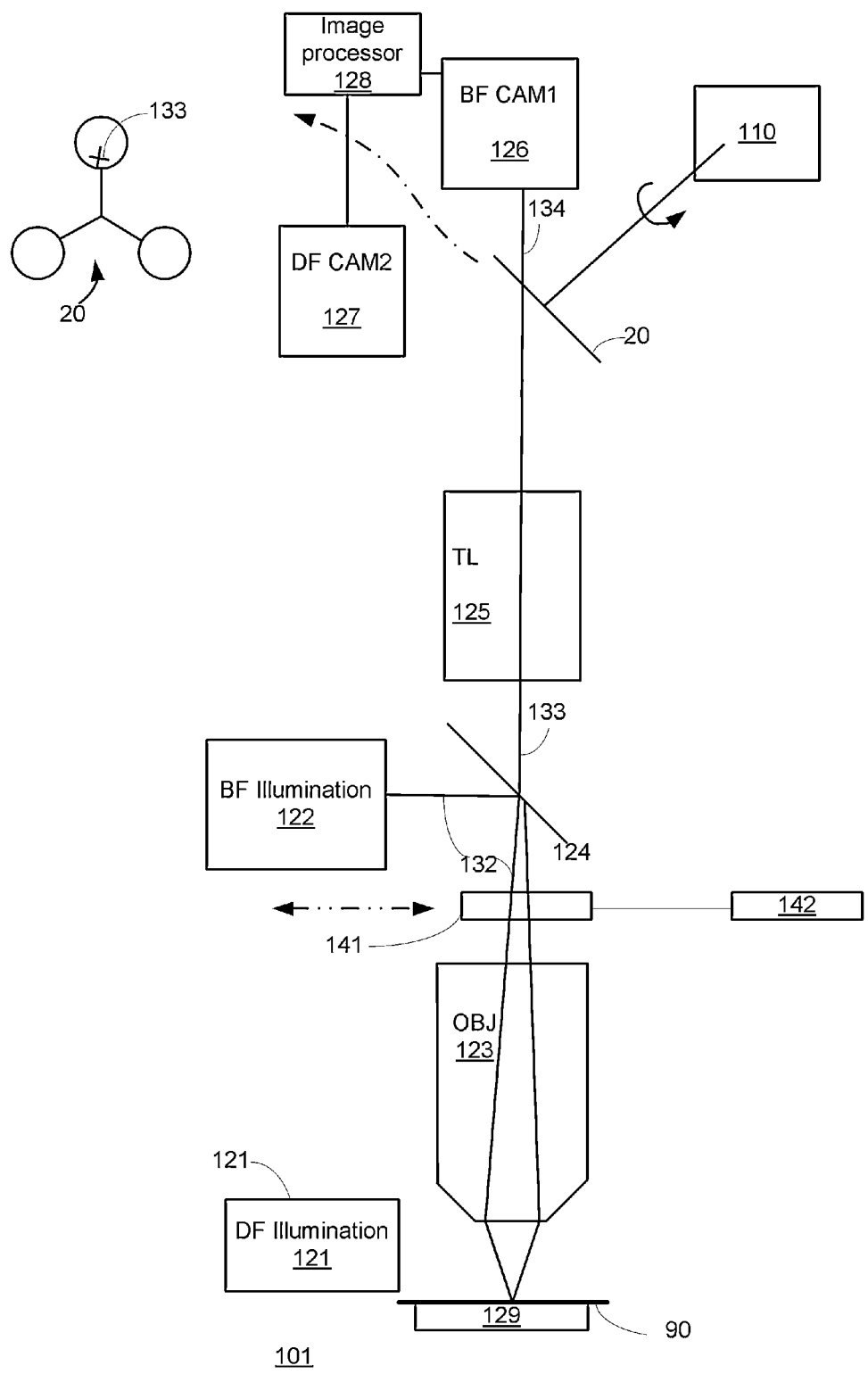
FIG. 6 illustrates a substrate and a multiple mode imager according to an embodiment of the invention.
Figure 7:
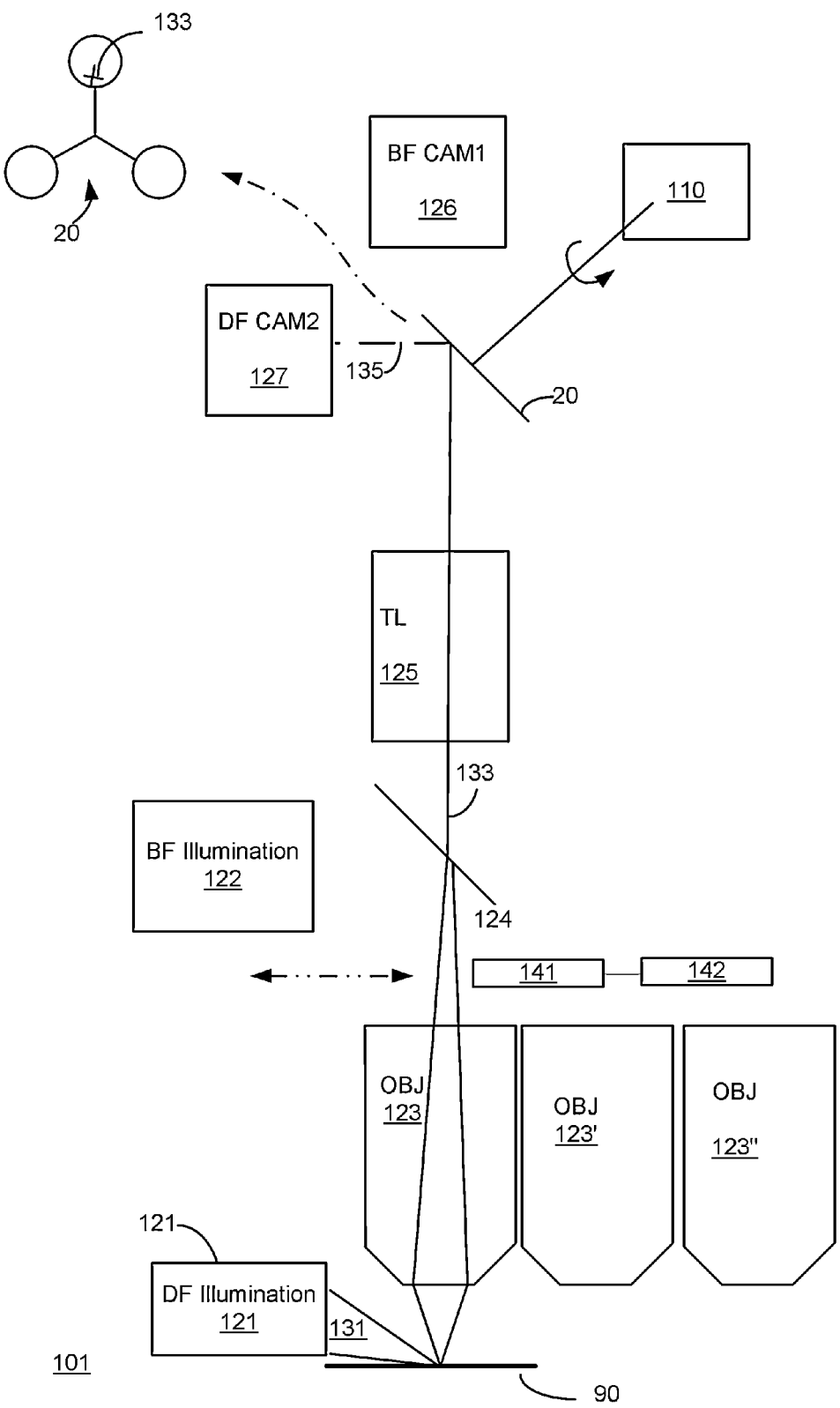
FIG. 7 illustrates a substrate and a multiple mode imager according to an embodiment of the invention.

FIGS. 6 and 7 illustrate a substrate 90 and a multiple mode imager 101 according to an embodiment of the invention.

The multiple mode imager of FIGS. 6 and 7 differs from the multiple mode imager of FIGS. 3 and 4 by including a second movable optical element 141 in addition to the first movable optical element (such as mirror 20).

The movable optical element 141 is illustrated as reciprocating (by optical element movement module 142) between a first position in which it is within the collection path 133 (FIG. 6) and between a second position in which it is outside the collection path 133 (FIG. 7) or any relevant optical path.

It is noted that the reciprocating of FIGS. 6 and 7 may involve moving the second movable optical element 141 along a linear path in which the angle between the second movable optical element 141 and the substrate remains the same (parallel or non-parallel relationship) but other movement may be provided.

FIG. 6 illustrates a collection of radiation by bright field camera BF CAM1 126. FIG. 7 illustrates a collection of radiation by dark field camera DF CAM2 127. Any other combination of movement of the first and second movable optical elements may be provided. Yet for another example in both modes radiation may be split between the cameras (for example using a beam splitter).

Figure 8:
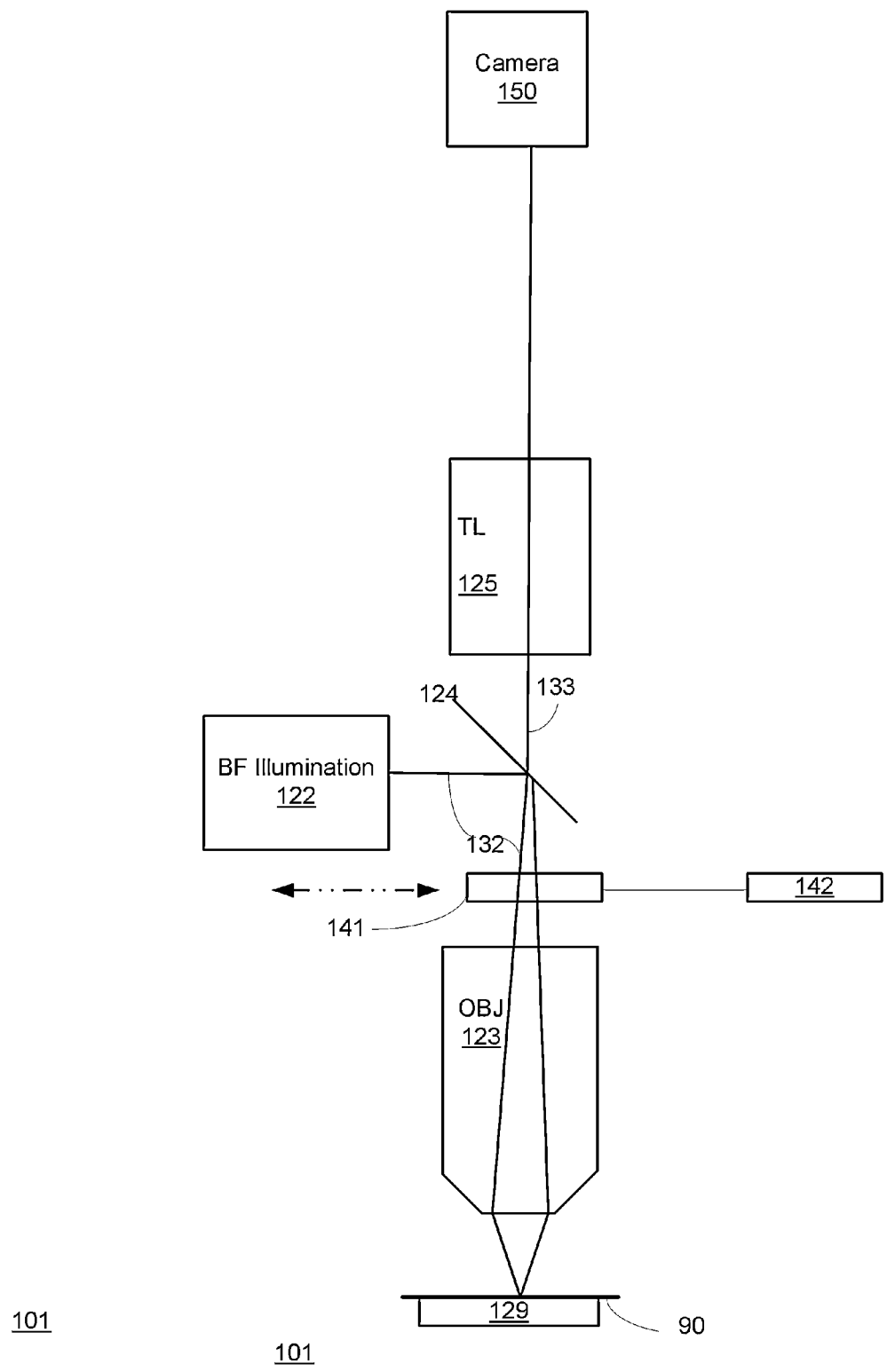
FIG. 8 illustrates a substrate and a multiple mode imager according to an embodiment of the invention.

FIG. 8 illustrates a substrate 90 and a multiple mode imager 101 according to an embodiment of the invention.

The multiple mode imager of FIG. 8 differs from the multiple mode imager of FIGS. 6-7 by including a single camera 150 (instead of BF CAM1 126 and DF CAM2 127) and by not including the first movable optical element (denoted 20 in FIGS. 6 and 7).

The alternating between the optical modes is obtained by the reciprocal movement of the second movable optical element 141.

Figure 9:
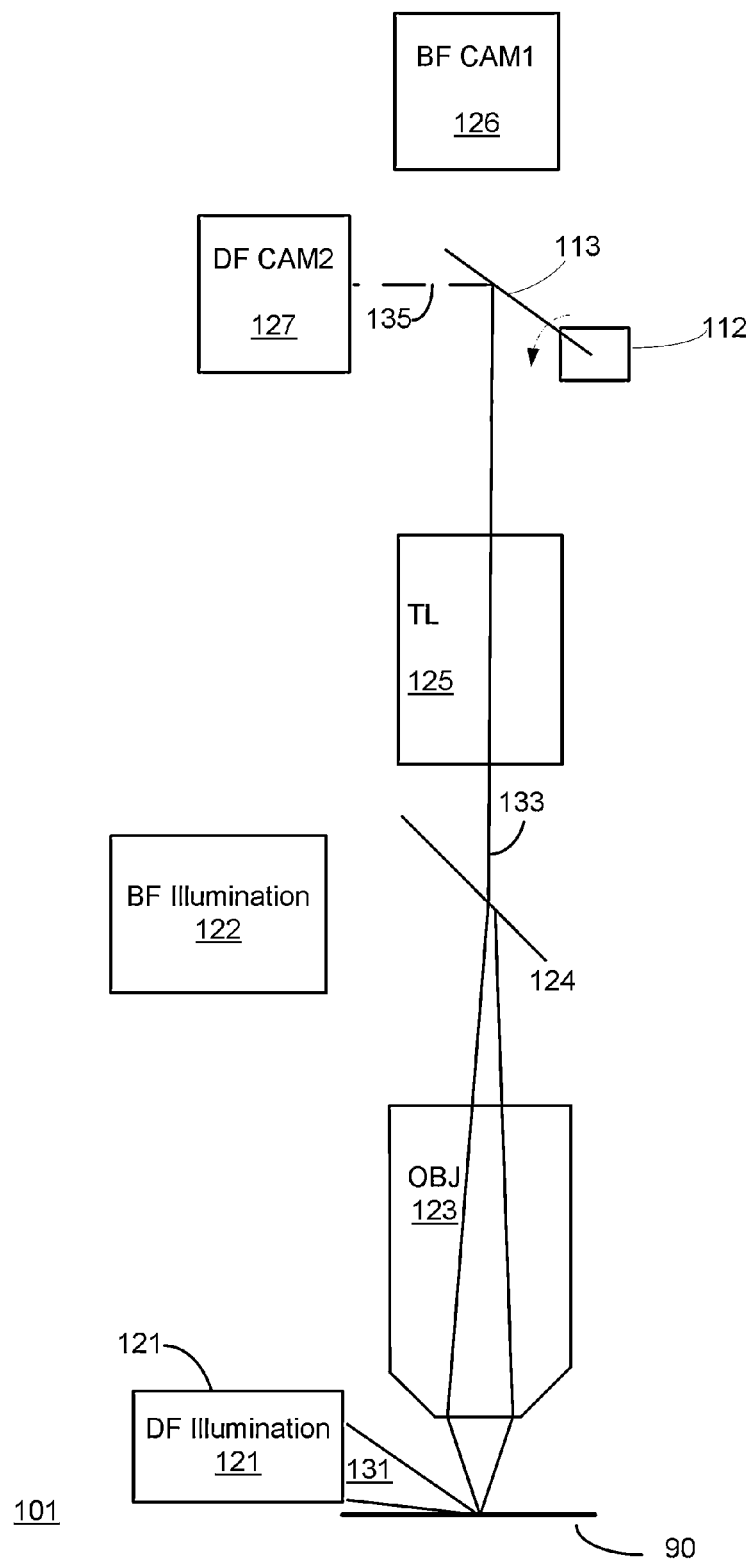
FIG. 9 illustrates a substrate and a multiple mode imager according to an embodiment of the invention.
Figure 10:
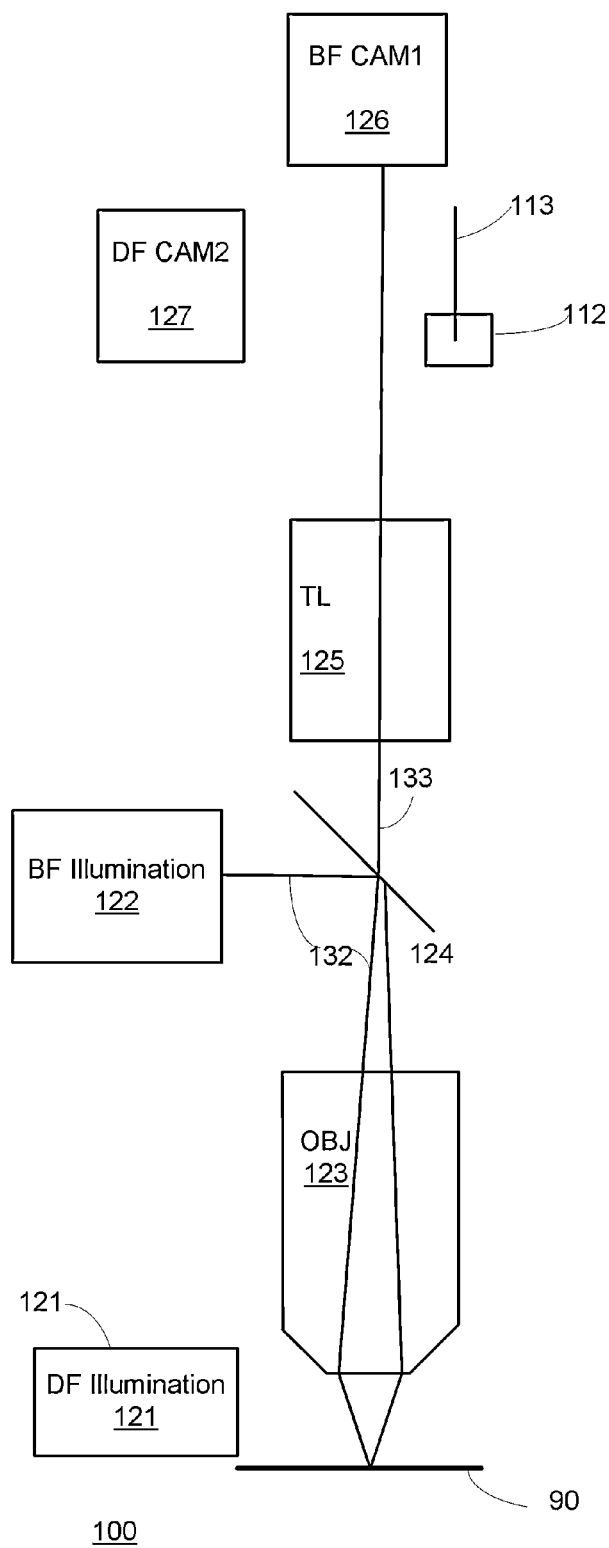
FIG. 10 illustrates a substrate and a multiple mode imager according to an embodiment of the invention.
Figure 11:
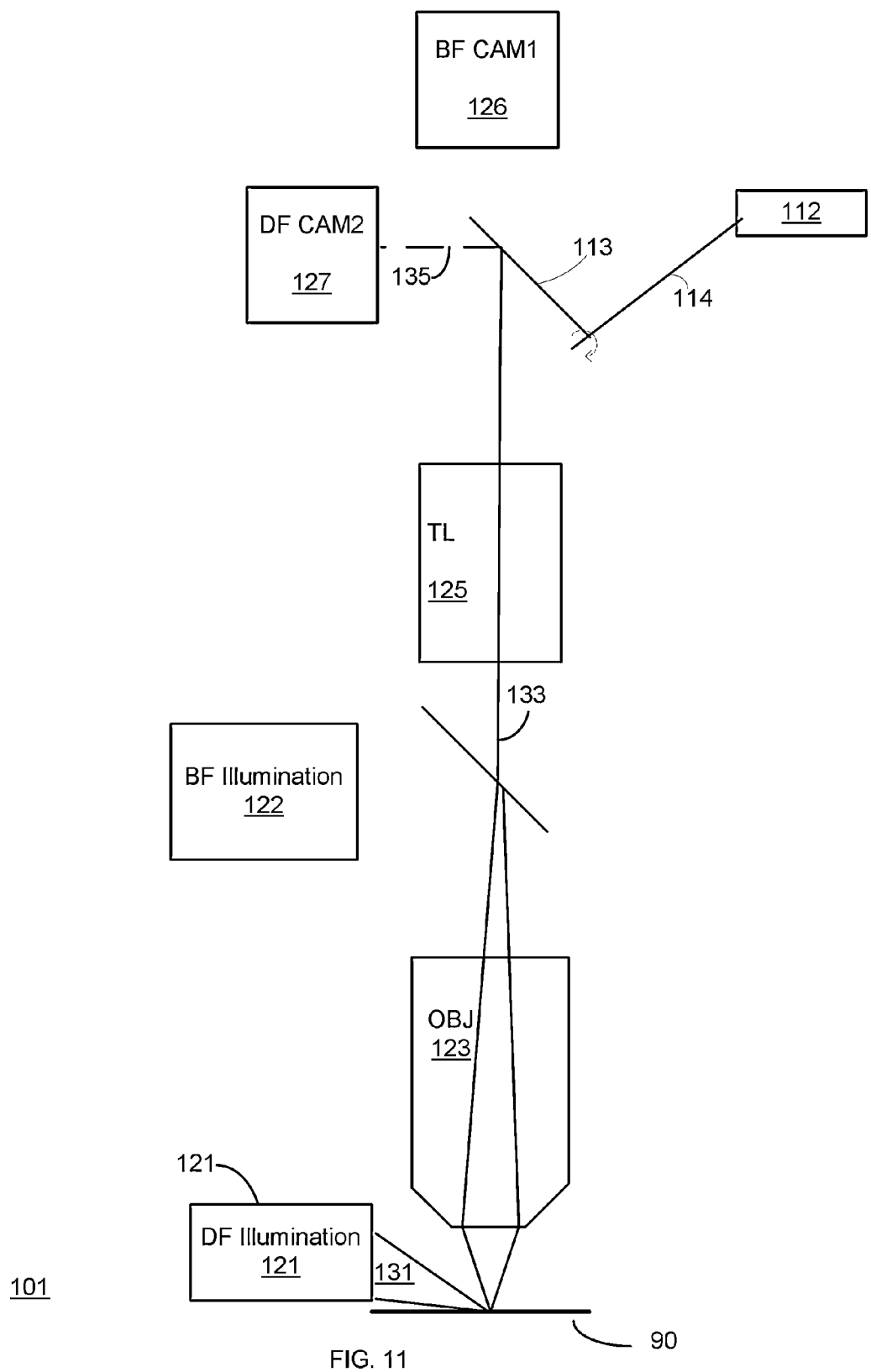
FIG. 11 illustrates a substrate and a multiple mode imager according to an embodiment of the invention.

FIGS. 9-11 illustrate a substrate 90 and a multiple mode imager 101 according to an embodiment of the invention.

The multiple mode imager of FIGS. 9-11 differs from the multiple mode imager of FIGS. 6-7 by including a third movable optical element 113 instead of the first movable optical element 20 of FIGS. 6 and 7.

Figure 12:
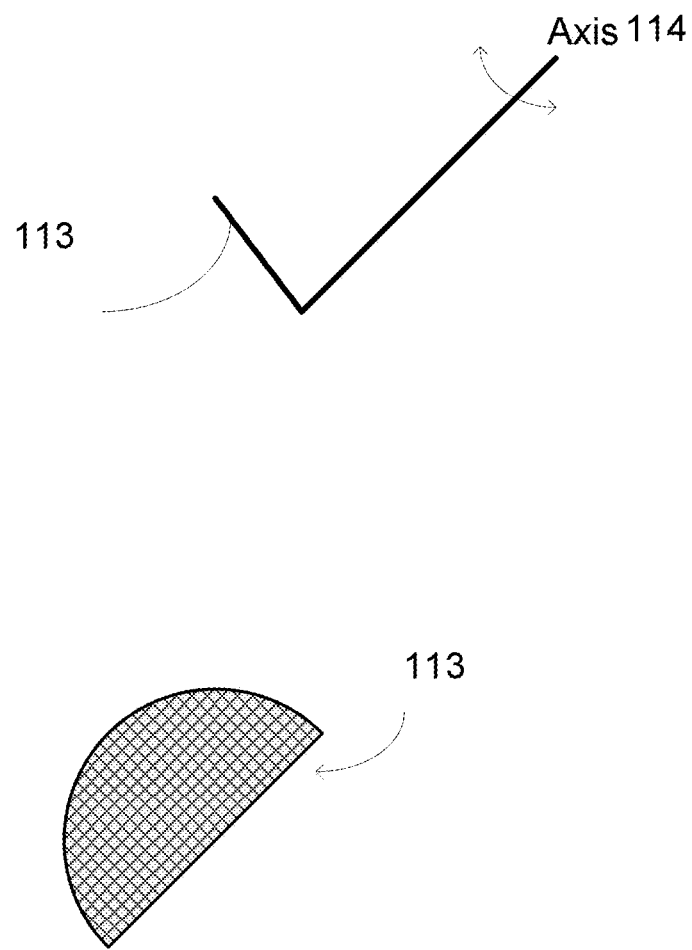
FIG. 12 illustrates various components of a multiple mode imager according to an embodiment of the invention.

While the first movable element was rotated about an axis that was oriented in relation the substrate and to the collection axis 133 and was within a virtual plane formed by the pages of FIGS. 6-7, the third movable optical element 113 of FIGS. 9 and 10 may be rotated about an axis that is parallel to the substrate and to the collection axis 133 and is normal to a virtual plane formed by the pages of FIGS. 9-10. The third movable optical element 113 of FIG. 11 may be rotated about an axis 114 that is oriented in relation the substrate and to the collection axis 133 and is within a virtual plane formed by the page of FIG. 11, wherein the axis 114 is connected to an edge of the third movable optical element 113. FIG. 12 illustrates the third movable element as being a mirror having a semi-circular shape.

The third movable optical element 113 may be moved (by optical element movement module 112) between a first position (FIG. 9) in which is outside the collection path 133 and allows the radiation to impinge on BF CAM1 126 and between a second position (FIGS. 10 and 11) in which it directs the radiation towards DF CAM2 127.

The movement may change the angle between the substrate 90 and the third movable optical element 113.

Figure 13:
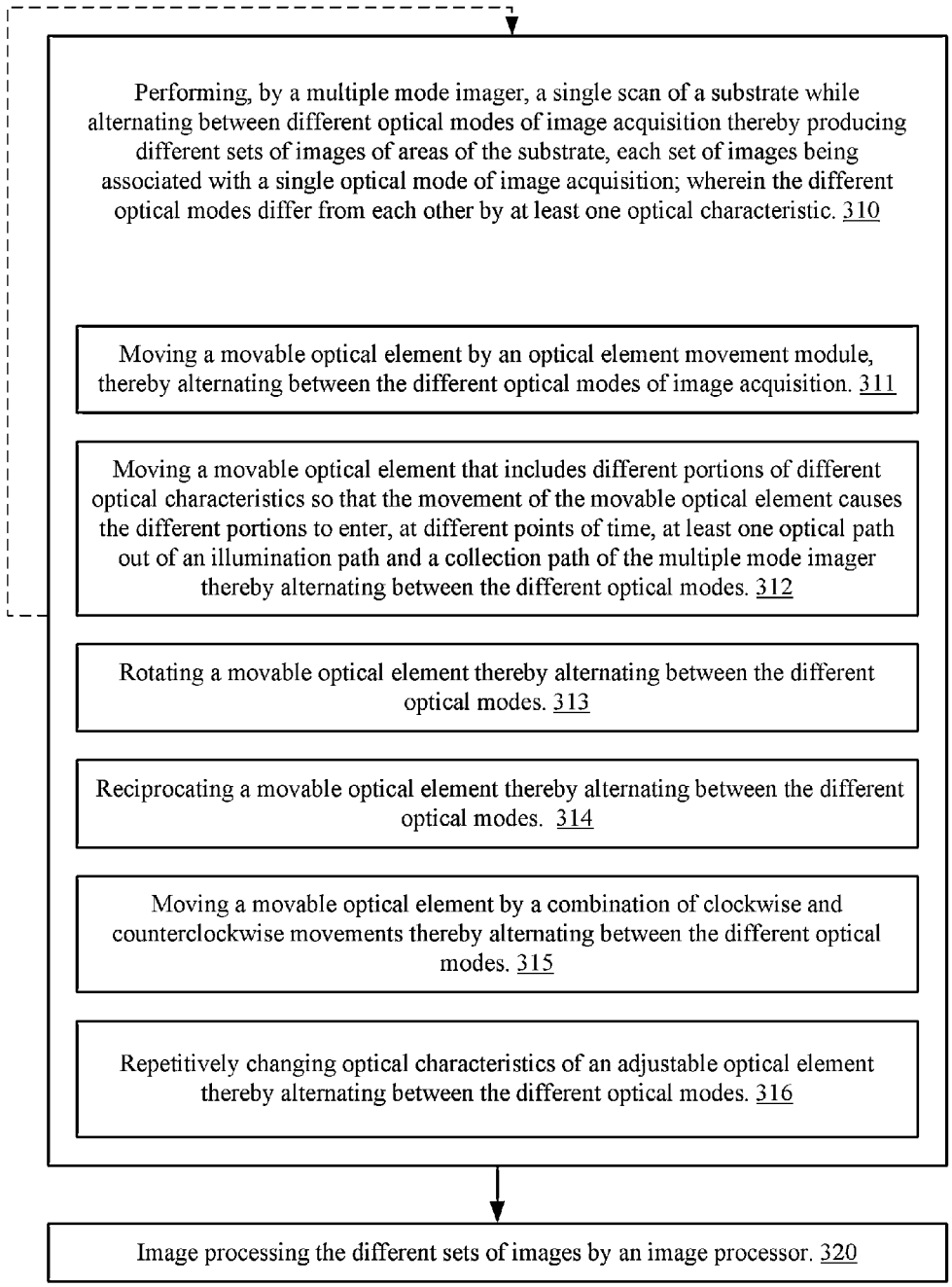
FIG. 13 illustrates a method according to an embodiment of the invention.

FIG. 13 illustrates method 300 according to an embodiment of the invention.

Method 300 for multiple mode evaluation may start by stage 310 of performing, by a multiple mode imager, a single scan of a substrate while alternating between different optical modes thereby producing different sets of images of areas of the substrate, each set of images being associated with a single optical mode of image acquisition; wherein the different optical modes differ from each other by at least one optical characteristic.

The different sets of images may cover overlapping areas of the substrate. Each point of the substrate may be associated with a pixel per each of the different optical modes.

At least two optical modes (of the different optical modes) may differ from each other by at least one out of polarization, angular coverage (collection angle, illumination angle, both collection and illumination angles, bright field, dark field and the like), wavelength, intensity or any other optical parameter.

The number of cameras of the multiple mode imager may equal the number of different optical modes or may differ from the number of different optical modes.

Stage 310 may include at least one of the following:
a. Moving (311) a movable optical element by an optical element movement module, thereby alternating between the different optical modes of image acquisition.
b. Moving (312) a movable optical element that includes different portions of different optical characteristics so that the movement of the movable optical element causes the different portions to enter, at different points of time, at least one optical path out of an illumination path and a collection path of the multiple mode imager thereby alternating between the different optical modes.
c. Rotating (313) a movable optical element thereby alternating between the different optical modes. (See, for example mirrors 10 and 20 of FIGS. 1 and 2 and the rotating of mirror 20 in FIGS. 3, 4, 6 and 7). Either one of mirrors 10 and 20 is also referred to as first movable optical element.
   i. The rotating may cause placing, at different points of time, different portions of the movable optical element having different optical characteristics within at least one of a collection path and an illumination path of the multiple mode imager thereby alternating between the different optical modes.
   ii. The different portions of the movable optical element may differ from each other by at least one out of polarization, reflectivity, wavelength filtering, spatial filtering, attenuation and the like. See for example FIGS. 1, 2 and 12.
   iii. The movable optical element may include a center and multiple spaced apart branches that extend from the center. Each branch may include a radiation reflecting element. See for example FIGS. 1 and 2.
   iv. The rotation of the movable optical element causes radiation reflecting elements attached to the spaced apart branches to enter, during only some of the different points of time, at least one optical path out of an illumination path and a collection path of the multiple mode imager. See for example FIGS. 3, 4, 6 and 7.
   v. Each radiation reflecting element, when entering the collection path directs radiation from the substrate towards a first camera of the multiple mode imager; wherein when any radiation reflecting element of the movable optical element may be not positioned within the collection path the radiation from the substrate may be directed towards a second camera of the multiple mode imager. See, for example, FIGS. 2, 4, 6 and 7.

vi. The first and second cameras may include a dark field camera and a bright field camera. See, for example, FIGS. 2, 4, 6 and 7.

vii. The number of spaced apart branches may two, three and the like. See for example, FIGS. 1 and 2. It is noted that the number of branches may include one, two, three or may exceed three branches.

viii. The spaced apart branches may be arranged in radial symmetry.

ix. The movable optical element may include a center and multiple spaced apart radiation reflecting elements, wherein movable optical element defines gaps between the spaced apart radiation reflecting elements. A rotation of the movable optical element may cause radiation reflecting elements attached to the spaced apart branches to enter, during only some of the different points of time, at least one optical path out of an illumination path and a collection path of the multiple mode imager. See, for example, FIGS. 2 and 4-7.

d. Reciprocating (314) a movable optical element thereby alternating between the different optical modes. See, for example, second movable optical element 141 of FIGS. 6-8. Yet for another example see third movable optical element 113 of FIGS. 9-11.

i. The moveable optical element may be moved between a first position in which the movable optical element may be outside an optical path out of a collection path and an illumination path of the multiple mode imager and a second position in which the movable optical element may be within the optical path.

ii. The first and second positions may differ from each other by an angle between the movable optical element and the substrate. See, for example, third movable optical element 113 of FIGS. 9-11.

iii. The movable optical element may be moved, while alternating the optical modes, by a linear movement that does not change that angle between the substrate and the movable optical element. See, for example the second movable optical element 141 of FIGS. 6-8.

e. Moving (315) a movable optical element by a combination of clockwise and counterclockwise movements thereby alternating between the different optical modes. See, for example, third movable optical element 113 of FIGS. 9-11.

i. The movable optical element may be a mirror.

ii. The mirror may have a semi-circle shape or any other shape.

f. Repetitively (316) changing optical characteristics of an adjustable optical element thereby alternating between the different optical modes. See, for example adjustable optical element 400 of FIG. 14 that has adjustable optical characteristics (such as reflectivity and transparency) and may repetitively alternate between being transparent and reflective so that light reaches BF CAM1 126 and DF CAM2 127 and different points of time.

Stage 310 may be followed by stage 320 of image processing the different sets of images by an image processor. The image processing may include combining images of different sets of images to provide a combined image. There may be provide an image processor per each camera but the number of image processors may differ from the number of cameras. See, for example FIG. 3 in which a single image processor 128 processes images of both cameras 127 and 128.

If a new scan is required then stage 310 may also be followed by itself.

Figure 15:
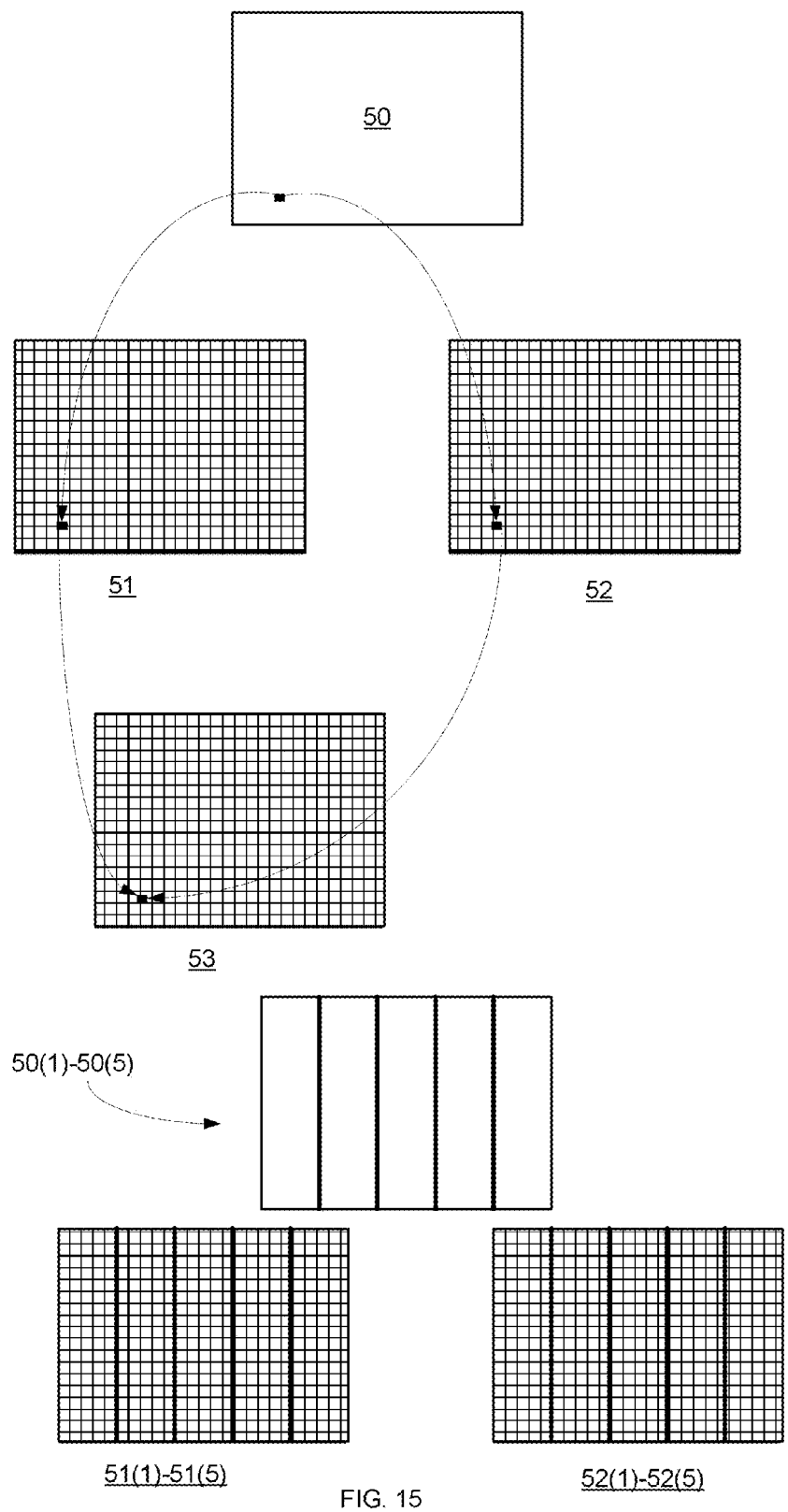
FIG. 15 illustrates a substrate and various images according to various embodiments of the invention.

FIG. 15 illustrates a substrate 50 and various images according to an embodiment of the invention.

Assuming that during a single scan the entire substrate is scanned and that the multiple mode imager alternates between two optical modes then images 51 and 52 (each of the entire substrate) are acquired—one for each optical mode. Small black boxes in FIG. 15 illustrate that a point (or a multiple point region) is represented by pixels at each of images 51 and 52.

Images 51 and 52 (for example dark field and bright field images) may represented by a combined image 53 in which each pixel (of the combined image) includes information (pixels) from both images 51 and 52.

FIG. 15 also illustrates a scenario in which five different scans are required for imaging the entire substrate. The first till fifth scans image selected portions of the substrate such as stripes 50(1)-50(5) so that two sets of images 51(1)-51(5) and 52(1)-52(5) are formed. These sets of images may be combined.

It is noted that the multiple mode imager may scan only a portion of the substrate and that if it alternates between more than two optical modes then more than two images are acquired during a single scan.

In the foregoing specification, the invention has been described with reference to specific examples of embodiments of the invention. It will, however, be evident that various modifications and changes may be made therein without departing from the broader spirit and scope of the invention as set forth in the appended claims.

Those skilled in the art will recognize that boundaries between the functionality of the above described operations are merely illustrative. The functionality of multiple operations may be combined into a single operation, and/or the functionality of a single operation may be distributed in additional operations. Moreover, alternative embodiments may include multiple instances of a particular operation, and the order of operations may be altered in various other embodiments.

Thus, it is to be understood that the architectures depicted herein are merely exemplary, and that in fact many other architectures can be implemented which achieve the same functionality. In an abstract, but still definite sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality.

However, other modifications, variations, and alternatives are also possible. The specifications and drawings are, accordingly, to be regarded in an illustrative rather than in a restrictive sense.

The word "comprising" does not exclude the presence of other elements or steps then those listed in a claim. It is understood that the terms so used are interchangeable under appropriate circumstances such that the embodiments of the invention described herein are, for example, capable of operation in other orientations than those illustrated or otherwise described herein.

Furthermore, the terms "a" or "an," as used herein, are defined as one or more than one. Also, the use of introductory phrases such as "at least one" and "one or more" in the claims should not be construed to imply that the introduction of another claim element by the indefinite articles "a" or "an" limits any particular claim containing such introduced claim element to inventions containing only one such element, even when the same claim includes the introductory phrases "one or more" or "at least one" and indefinite articles such as "a" or "an." The same holds true for the use of definite articles. Unless stated otherwise, terms such as "first" and "second" are used to arbitrarily distinguish between the elements such terms describe.

Thus, these terms are not necessarily intended to indicate temporal or other prioritization of such elements. The mere fact that certain measures are recited in mutually different claims does not indicate that a combination of these measures cannot be used to advantage.

I claim:

1. A multiple mode evaluation system, comprising:
   a multiple mode imager that comprises at least one camera; a dark field illumination source; a bright field illumination source; a movable optical element and an optical element movement module;
   wherein the multiple mode evaluation system is arranged to perform a single scan of the substrate while alternating between different optical modes thereby producing, by the at least one camera, different sets of images of areas of the substrate, each set of images being associated with a single optical mode of image acquisition; wherein the different optical modes differ from each other by at least one optical characteristic that is not a wavelength and comprise a dark field illumination mode and a bright field illumination mode;
   wherein the dark field illumination source is activated only when the multiple mode imager operates at the dark field illumination mode;
   wherein the bright field illumination source is activated only when the multiple mode imager operates at the bright field illumination mode;
   wherein the optical element movement module is connected to the movable optical element and is arranged to move the movable optical element;
   wherein the movable optical element comprises a center and multiple spaced apart branches that extend from the center, wherein each branch comprises a radiation reflecting element;
   wherein a rotation of the movable optical element (a) causes, when the multiple mode imager operates at the bright field illumination mode, one of the radiation reflecting elements attached to the spaced apart branches to enter a collection path of the multiple mode imager; and (b) causes, when the multiple mode imager operates at the dark field illumination mode, each one of the radiation reflecting elements attached to the spaced apart branches to be outside the collection path of the multiple mode imager.

2. The multiple mode evaluation system according to claim 1 further comprising an image processor that is arranged to generate combined images from images that belong to different sets of images.

3. The multiple mode evaluation system according to claim 1 comprising acquiring only a single image per optical mode of the different optical modes before changing to another optical mode of the different optical modes.

4. A method for multiple mode evaluation, the method comprises:
   performing, by a multiple mode imager that comprises at least one camera a dark field illumination source; a bright field illumination source; a movable optical element and an optical element movement module, a single scan of a substrate while alternating between different optical modes thereby producing, by the at least one camera, different sets of images of areas of the substrate, each set of images being associated with a single optical mode of image acquisition;
   wherein the different optical modes differ from each other by at least one optical characteristic that is not a wavelength and comprise a dark field illumination mode and a bright field illumination mode;
   wherein the performing of the single scan of the substrate while alternating between the different optical modes comprises:
   activating the dark field illumination source only when the multiple mode imager operates at the dark field illumination mode;
   activating the bright field illumination source only when the multiple mode imager operates at the bright field illumination mode; and
   rotating the movable optical element by the optical element movement module that is connected to the movable optical element;
   wherein the movable optical element comprises a center and multiple spaced apart branches that extend from the center, wherein each branch comprises a radiation reflecting element;
   wherein the rotating of the movable optical element (a) causes, when the multiple mode imager operates at the bright field illumination mode, one of the radiation reflecting elements attached to the spaced apart branches to enter a collection path of the multiple mode imager; and (b) causes, when the multiple mode imager operates at the dark field illumination mode, each one of the radiation reflecting elements attached to the spaced apart branches to be outside the collection path of the multiple mode imager.

5. A multiple mode evaluation system, comprising:
   a multiple mode imager that comprises at least one camera; a dark field illumination source; a bright field illumination source; a movable optical element and an optical element movement module;
   wherein the multiple mode evaluation system is arranged to perform a single scan of the substrate while alternating between different optical modes thereby producing, by the at least one camera, different sets of images of areas of the substrate, each set of images being associated with a single optical mode of image acquisition; wherein the different optical modes differ from each other by at least one optical characteristic that is not a wavelength and comprise a dark field illumination mode and a bright field illumination mode;
   wherein the dark field illumination source is activated only when the multiple mode imager operates at the dark field illumination mode;
   wherein the bright field illumination source is activated only when the multiple mode imager operates at the bright field illumination mode;
   wherein the optical element movement module is connected to the movable optical element and is arranged to move the movable optical element;

wherein the movable optical element comprises a center and multiple spaced apart branches that extend from the center, wherein each branch comprises a radiation reflecting element;

wherein a rotation of the movable optical element (a) causes, when the multiple mode imager operates at the dark field illumination mode, one of the radiation reflecting elements attached to the spaced apart branches to enter a collection path of the multiple mode imager; and (b) causes, when the multiple mode imager operates at the bright field illumination mode, each one of the radiation reflecting elements attached to the spaced apart branches to be outside the collection path of the multiple mode imager.

\* \* \* \* \*